US008779145B2

(12) United States Patent
Elenbaas

(10) Patent No.: US 8,779,145 B2
(45) Date of Patent: Jul. 15, 2014

(54) PROCESS FOR THE PREPARATION OF 2-(CYCLOHEXYLMETHYL)-N-{2-[(2S)-1-METHYLPYRROLIDIN-2-YL]ETHYL}-1,2,3,4-TETRAHYDROISOQUINOLINE

(75) Inventor: Steven Elenbaas, Bridgewater, NJ (US)

(73) Assignee: Sanofi, Paris (FR)

( * ) Notice: Subject to any disclaimer, the term of this patent is extended or adjusted under 35 U.S.C. 154(b) by 46 days.

(21) Appl. No.: 13/600,975

(22) Filed: Aug. 31, 2012

(65) Prior Publication Data

US 2013/0137718 A1    May 30, 2013

Related U.S. Application Data

(63) Continuation of application No. PCT/US2011/027118, filed on Mar. 4, 2011.

(60) Provisional application No. 61/311,069, filed on Mar. 5, 2010.

(30) Foreign Application Priority Data

Nov. 25, 2010 (FR) ..................................... 10 59750

(51) Int. Cl.
*C07D 401/12* (2006.01)
(52) U.S. Cl.
CPC .................................... *C07D 401/12* (2013.01)
USPC ........................................................ 546/150
(58) Field of Classification Search
None
See application file for complete search history.

(56) References Cited

U.S. PATENT DOCUMENTS

| 4,228,170 | A | 10/1980 | Bondinell et al. |
| 4,315,935 | A | 2/1982 | Ali |
| 4,857,301 | A | 8/1989 | Czarniecki et al. |
| 5,750,520 | A | 5/1998 | Danilewicz et al. |
| 6,414,149 | B1 | 7/2002 | Chu-Moyer et al. |
| 6,562,828 | B1 | 5/2003 | Katoh et al. |
| 6,562,978 | B1 | 5/2003 | Imamura et al. |
| 6,677,349 | B1 | 1/2004 | Griesgraber |
| 7,833,999 | B2 | 11/2010 | Diaz Martin et al. |
| 7,858,619 | B2 | 12/2010 | Hofmeister et al. |
| 8,273,733 | B2 | 9/2012 | Diaz Martin et al. |
| 2001/0034352 | A1 | 10/2001 | Peglion et al. |
| 2002/0165251 | A1 | 11/2002 | Caldirola et al. |
| 2003/0027836 | A1 | 2/2003 | Matsui et al. |
| 2005/0043304 | A1 | 2/2005 | Kato et al. |
| 2005/0267146 | A1 | 12/2005 | Xue et al. |
| 2006/0167023 | A1 | 7/2006 | Jolidon et al. |
| 2007/0105834 | A1 | 5/2007 | Diaz Martin et al. |
| 2012/0149728 | A1 | 6/2012 | Langevin et al. |
| 2012/0323003 | A1 | 12/2012 | Diaz Martin et al. |

FOREIGN PATENT DOCUMENTS

| EP | 0300725 A1 | 1/1989 |
| EP | 1072596 A2 | 1/2001 |
| EP | 1122252 A1 | 8/2001 |
| WO | 94/29273 A1 | 12/1994 |
| WO | 00/07993 A1 | 2/2000 |
| WO | 01/74808 A1 | 10/2001 |
| WO | 02/076925 A2 | 10/2002 |
| WO | 03/055848 A2 | 7/2003 |
| WO | 03/074051 A1 | 9/2003 |
| WO | 2004/094371 A2 | 11/2004 |
| WO | 2005/008037 A1 | 1/2005 |
| WO | 2005/067502 A2 | 7/2005 |
| WO | 2005/070133 A2 | 8/2005 |
| WO | 2005/110409 A2 | 11/2005 |
| WO | 2005/118547 A1 | 12/2005 |
| WO | 2005/120505 A2 | 12/2005 |
| WO | WO2005/118547 A1 | 12/2005 |
| WO | 2006/018308 A1 | 2/2006 |
| WO | 2006/018309 A1 | 2/2006 |
| WO | 2006/024823 A1 | 3/2006 |
| WO | 2006/065216 A1 | 6/2006 |
| WO | 2006/067587 A2 | 6/2006 |
| WO | 2006/068826 A2 | 6/2006 |
| WO | 2006/122014 A2 | 11/2006 |
| WO | 2008/043544 A1 | 4/2008 |
| WO | 2009/127822 A2 | 10/2009 |
| WO | 2010/151611 A1 | 12/2010 |
| WO | 2011/109680 A2 | 9/2011 |

OTHER PUBLICATIONS

Elenbaas, FR 1059750 filed Nov. 25, 2010, Ceritifed copy of priority document of PCT/US2011/027118.*
Grunewald G.L. et al., "3,7-Disubstituted-1,2,3,4-Tetrahydroisoquinolines Display Remarkable Potency and Selectivity as Inhibitors of Phenylethanolamine N-Methyltransferase Versus the a2-Adrenoceptor", Journal of Medicinal Chemistry 42(11):1982-1990 (1999).
Giovannini, Maria Grazia et al "Effects of histamine H3 receptor agonists and antagonists on cognitive performance and scopolamine-induced amnesia" Behavioural Brain Research (1999) vol. 104, pp. 147-155.
Blank, Benjamin et al "Inhibitors of Phenylethanolamine N-Methyltransferase and Epinephrine Biosynthesis. 2. 1,2,3,4-Tetrahydroisoquinoline-7-sulfonanilides" Journal of Medicinal Chemistry (1980) vol. 23, pp. 837-840.
Turner, Sean C. et al"A New Class of Histamine H3-Receptor Antagonists: Synthesis and Structure-Activity Relationships of 7,8,9,10-Tetrahydro-6H-cyclohepta[b]quinolines" Bioorganic & Medicinal Chemistry Letters (2003) vol. 13, pp. 2131-2135.
Tang, Guozhi et al "Pyrogallol-Based Molecules as Potent Inhibitors of the Antiapoptotic Bcl-2 Proteins" Journal of Medicinal Chemistry (2007) vol. 50 No. 8, pp. 1723-1726.
Ueno, Hiroshi et al "Synthesis and Structure-Activity Relationships of Novel Selective Factor Xa Inhibitors with a Tetrahydroisoquinoline Ring" Journal of Medicinal Chemistry (2005) vol. 48 No. 10, pp. 3586-3604.
Fish, Paul V. et al "Synthesis of 1,2,5,6-Tetrahydro-3-pyridinylalanine: A Key Intermediate in the Preparation of Thrombin Inhibitor UK-239,326" Synthetic Communications (2008) vol. 38 No. 16, pp. 2787-2798.

(Continued)

*Primary Examiner* — Zinna Northington Davis
(74) *Attorney, Agent, or Firm* — Scully, Scott, Murphy & Presser, P.C.; Kelly L. Bender, Esq.

(57) ABSTRACT

Industrially applicable process for preparing 2-(cyclohexyl-methyl)-N-{2-[(2S)-1-methylpyrrolidin-2-yl]ethyl}-1,2,3,4-tetrahydroisoquinoline-7-sulfonamide, and salts thereof.

18 Claims, No Drawings

(56) References Cited

OTHER PUBLICATIONS

Delucca, George V. et al "Discovery of CC Chemokine Receptor-3 (CCR3) Antagonists with Picomolar Potency" Journal of Medicinal Chemistry (2005) vol. 48 No. 6, pp. 2194-2211.

Palani, Anandan et al "Biaryl Ureas as Potent and Orally Efficacious Melanin Concentrating Hormone Receptor 1 Antagonists for the Treatment of Obesity" Journal of Medicinal Chemistry (2005) vol. 48 No. 15, pp. 4746-4749.

Brinner, Kristin M. et al "Potent 4-aminopiperidine based antimalarial agents" Bioorganic & Medicinal Chemistry Letters (2005) vol. 15 No. 2, pp. 345-348.

Grunewald, Gary L. et al "Synthesis, Biochemical Evaluation, and Classical and Three-Dimensional Quantitative Structure-Activity Relationship Studies of 7-Substituted-1,2,3,4-tetrahydroisoquinolines and Their Relative Affinities toward Phenylethanolamine N-Methyltransferase and the a2-Adrenoceptor" Journal of Medicinal Chemistry (1999) vol. 42, pp. 118-134.

Debenneville, Peter L. et al "The Behavior of Aliphatic Aldehydes in the Leuckart-Wallach Reaction" J. Amer. Chem. Soc. (1950) vol. 72, pp. 3073-3075.

Clarke, C. B. et al "Decahydroisoquinolines and Related Compounds. Part II.* Some FurtherExamples of Abnormal Ultraviolet Absorption" Journal of the Chemical Society (1958) pp. 1967-1974.

U.S. Appl. No. 13/553,455, filed Jul. 19, 2012, Entitled: Process for the Preparation of 2-(Cyclohexylmethyl)-N-{2-[(2S)-1-Methylpyrrolidin-2-YL]Ethyl}-1,2,3,4-Tetrahydroisoquinoline-7-Sulfonamide, first named inventor Steven Elenbaas.

International Search Report dated Jun. 9, 2011 issued in PCT/US2011/027118.

* cited by examiner

PROCESS FOR THE PREPARATION OF 2-(CYCLOHEXYLMETHYL)-N-{2-[(2S)-1-METHYLPYRROLIDIN-2-YL]ETHYL}-1,2,3,4-TETRAHYDROISOQUINOLINE

CROSS-REFERENCE TO RELATED APPLICATIONS

This application is a CON. of PCT/US2011/027118 filed Mar. 4, 2011 which claims the benefit of U.S. Provisional Application No. 61/311,069 field on Mar. 5, 2010.

FIELD OF THE INVENTION

The present invention relates to processes for preparing 2-(cyclohexylmethyl)-N-{2-[(2S)-1-methylpyrrolidin-2-yl]ethyl}-1,2,3,4-tetrahydroisoquinoline-7-sulfonamide, various intermediates thereto and pharmaceutically acceptable salts thereof.

BACKGROUND OF THE INVENTION

The histamine H3 receptors are found in the central and peripheral nervous systems. The administration of histamine H3 receptor ligands may influence the secretion of neurotransmitters in the brain and the periphery and thus can be useful in the treatment of several disorders, including Alzheimer's disease and other dementias, obesity, central nervous system disorders such as vigilance and sleep disorders, narcolepsy, Parkinson's disease, attention-deficit hyperactivity disorder, memory and learning disorders, epilepsy, schizophrenia, moderate cognitive disorders, depression, anxiety, cardiovascular disorders, and gastrointestinal disorders.

To illustrate, a number of studies in the literature have demonstrated the cognitive enhancing properties of histamine H3 receptors antagonists in rodent models (See, e.g., Giovanni et al., *Behav. Brain Res.*, 1999, 104, 147-155). These reports further suggest that antagonists and/or inverse agonists could be useful for the treatment of cognitive impairments in neurological diseases such as Alzheimer's disease and related neurodegenerative disorders. Alzheimer's disease is the most common cause of dementia in the elderly, and is often characterized with one or more symptoms such as memory loss, confusion, irritability and aggression, mood swings, language breakdown, long-term memory loss, withdrawal of the sufferer, and loss of motor control.

2-(Cyclohexylmethyl)-N-{2-[(2S)-1-methylpyrrolidin-2-yl]ethyl}-1,2,3,4-tetrahydroisoquinoline-7-sulfonamide, which has the structure of Formula (I):

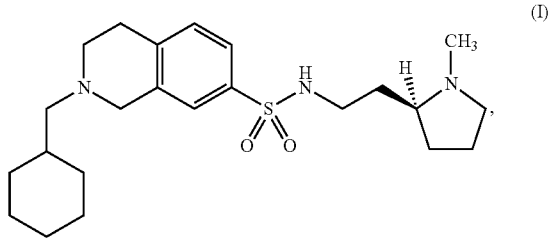 [SMILES: CN1CCC[C@H]1CCNS(=O)(=O)c1ccc2c(c1)CN(CC1CCCCC1)CC2]

(I)

is a potent histamine H3 receptor antagonist with inverse agonist properties. The preparation, physical properties and beneficial pharmacological properties of 2-(cyclohexylmethyl)-N-{2-[(2S)-1-methylpyrrolidin-2-yl]ethyl}-1,2,3,4-tetrahydroisoquinoline-7-sulfonamide are described in, for example, WO2005/118547 (also US2007/0105834).

WO2005/118547 describes a general method of synthesis which is difficult to transpose to the industrial scale for production in large quantities. This method of synthesis entails reacting 2-(2,2,2-trifluoroacetyl)-1,2,3,4-tetrahydro-isoquinoline-7-sulfonyl chloride with (+/−)-2-(2-aminoethyl)-1-methylpyrrolidine, which product is deprotected in methanol and hydrochloric acid. The enantiomers are next separated by chiral chromatography. The resulting N-{2-[(2S)-1-methylpyrrolidin-2-yl]ethyl}-1,2,3,4-tetrahydroisoquinoline-7-sulfonamide undergoes reductive amination with cyclohexanecarboxaldehyde in the presence of a palladium catalyst. 2-(Cyclohexylmethyl)-N-{2-[(2S)-1-methylpyrrolidin-2-yl]ethyl}-1,2,3,4-tetrahydroisoquinoline-7-sulfonamide is isolated as the free base and converted to a salt.

The present invention makes it possible to optimize the synthesis of 2-(cyclohexylmethyl)-N-{2-[(2S)-1-methylpyrrolidin-2-yl]ethyl}-1,2,3,4-tetrahydroisoquinoline-7-sulfonamide for industrial use by avoiding the chiral chromatographic separation of the enantiomers of (+/−)-N-[2-(1-methylpyrrolidin-2-yl)ethyl]-1,2,3,4-tetrahydroisoquinoline-7-sulfonamide and by providing a more direct synthesis.

BRIEF SUMMARY OF THE INVENTION

Accordingly, the present invention provides a process for producing 2-(cyclohexylmethyl)-N-{2-[(2S)-1-methylpyrrolidin-2-yl]ethyl}-1,2,3,4-tetrahydroisoquinoline-7-sulfonamide and salts thereof, of high purity and in a relatively high yield suitable for use on an industrial scale.

The present invention is also directed to synthetic intermediates, for example 2-cyclohexylmethyl-1,2,3,4-tetrahydroisoquinoline-7-sulfonyl chloride HX, a compound of Formula (II) given below, that are useful in the preparation of the 2-(cyclohexylmethyl)-N-{2-[(2S)-1-methylpyrrolidin-2-yl]ethyl}-1,2,3,4-tetrahydroisoquinoline-7-sulfonamide and salts thereof. The compound of Formula (II) is surprisingly stable as this compound contains a tertiary amine on the same molecule as a sulfonyl chloride substituent.

DETAILED DESCRIPTION OF THE INVENTION

Definitions and Abbreviations

As used above, and throughout the description of the invention, the following abbreviations, unless otherwise indicated, shall be understood to have the following meanings:

EtOAc ethyl acetate
g gram
kg kilogram
L liter
mL milliliter
MTBE methyl t-butyl ether
NaBH(OAc)$_3$ sodium triacetoxyborohydride As used above, and throughout the description of the invention, the following terms, unless otherwise indicated, shall be understood to have the following meanings:

The term "2-cyclohexylmethyl-1,2,3,4-tetrahydroisoquinoline-7-sulfonyl chloride HX salt" refers to the salt of 2-cyclohexylmethyl-1,2,3,4-tetrahydroisoquinoline-7-sulfonyl chloride formed after the reaction of 2-cyclohexylmethyl-1,2,3,4-tetrahydroisoquinoline with excess chlorosulfonic acid. The 2-cyclohexylmethyl-1,2,3,4-tetrahydroisoquinoline-7-sulfonyl chloride HX salt may be a mixture of salts. For calculation purposes, one skilled in the art may regard the HX salt as an HCl salt.

The term "pharmaceutically acceptable" refers to those compounds, materials, compositions, carrier agents, bulking agents, solvents, diluents and other excipients which are, within the scope of sound medicinal judgment, suitable for contact with humans or other mammals without undue toxicity, irritation, allergic response and the like, commensurate with a reasonable benefit/risk ratio.

A process of the invention for preparing 2-(cyclohexylmethyl)-N-{2-[(2S)-1-methylpyrrolidin-2-yl]ethyl}-1,2,3,4-tetrahydroisoquinoline-7-sulfonamide, or a pharmaceutically acceptable salt thereof, or a solvate or hydrate of a pharmaceutically acceptable salt comprises:

a) reductively aminating 1,2,3,4-tetrahydroisoquinoline, or a salt thereof, with cyclohexanecarboxaldehyde to give 2-cyclohexylmethyl-1,2,3,4-tetrahydroisoquinoline, or a salt thereof;
b) reacting 2-cyclohexylmethyl-1,2,3,4-tetrahydroisoquinoline, or a salt thereof, with excess chlorosulfonic acid to give 2-cyclohexylmethyl-1,2,3,4-tetrahydroisoquinoline-7-sulfonyl chloride HX salt, and optionally recrystallizing the 2-cyclohexylmethyl-1,2,3,4-tetrahydroisoquinoline-7-sulfonyl chloride HX salt;
c) coupling 2-cyclohexylmethyl-1,2,3,4-tetrahydroisoquinoline-7-sulfonyl chloride HX salt with (−)-2-(2-aminoethyl)-1-methylpyrrolidine to form 2-(cyclohexylmethyl)-N-{2-[(2S)-1-methylpyrrolidin-2-yl]ethyl}-1,2,3,4-tetrahydroisoquinoline-7-sulfonamide;
d) optionally reacting 2-(cyclohexylmethyl)-N-{2-[(2S)-1-methylpyrrolidin-2-yl]ethyl}-1,2,3,4-tetrahydroisoquinoline-7-sulfonamide with a stoichiometric amount or an excess of a salt-forming acid in a solvent to form a salt or a hydrate or solvate thereof; and e) optionally recrystallizing the product of step d).

In one aspect of the invention, processes for preparing the 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof, or a solvate or hydrate of a pharmaceutically acceptable salt as well as intermediates that are useful for preparing such compounds are outlined in Scheme 1:

Scheme 1:

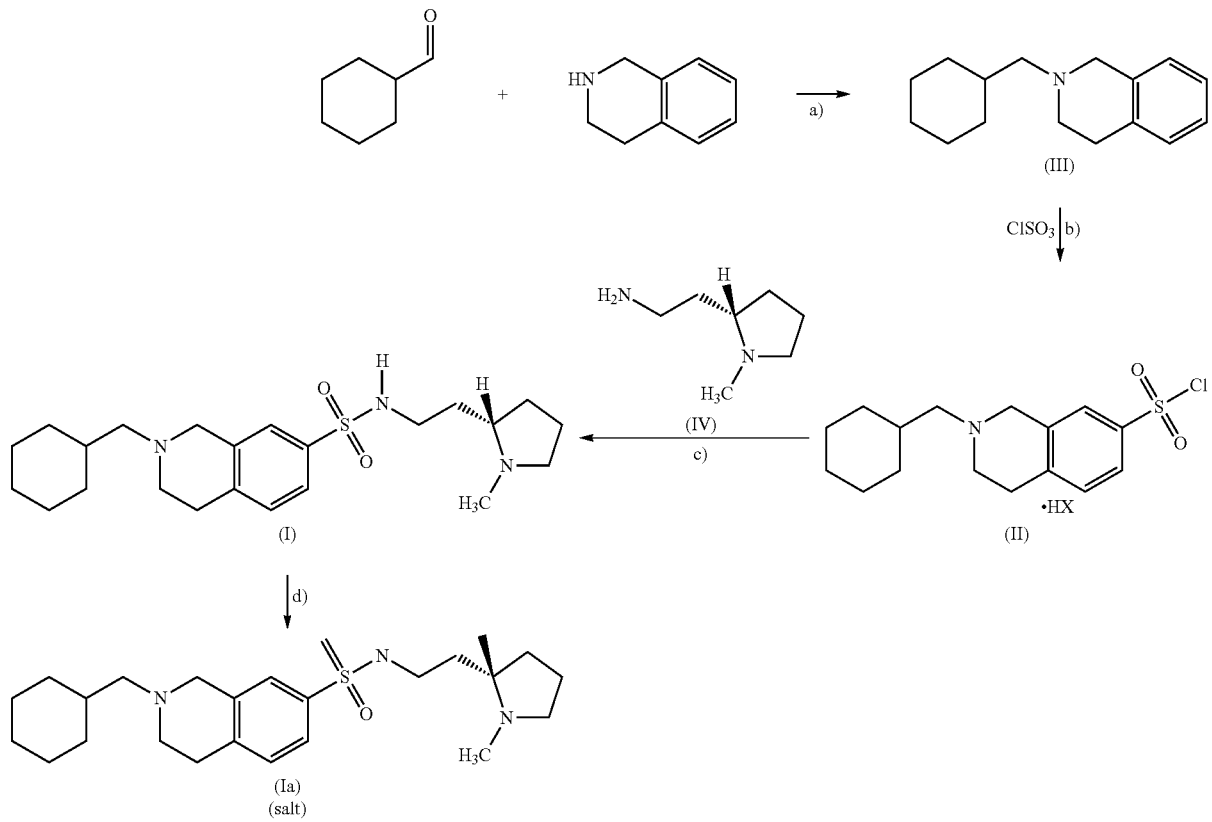

The processes for preparing 2-(cyclohexylmethyl)-N-{2-[(2S)-1-methylpyrrolidin-2-yl]ethyl}-1,2,3,4-tetrahydroisoquinoline-7-sulfonamide, or a pharmaceutically acceptable salt thereof, or a solvate or hydrate of a pharmaceutically acceptable salt, as outlined in Scheme 1 comprise:

a) reductively aminating 1,2,3,4-tetrahydroisoquinoline with cyclohexanecarboxaldehyde to give the compound of formula (III), 2-cyclohexylmethyl-1,2,3,4-tetrahydroisoquinoline, or a salt thereof;
b) reacting the compound of formula (III) with chlorosulfonic acid to give a compound of formula (II), 2-cyclohexylmethyl-1,2,3,4-tetrahydroisoquinoline-7-sulfonyl chloride HX salt, and optionally recrystallizing the compound of formula (II);
c) coupling the compound of formula (II) with (−)-2-(2-aminoethyl)-1-methylpyrrolidine to form a compound of formula (I), 2-(cyclohexylmethyl)-N-{2-[(2S)-1-methylpyrrolidin-2-yl]ethyl}-1,2,3,4-tetrahydroisoquinoline-7-sulfonamide,
d) optionally reacting the compound of formula (I) with a stoichiometric amount or an excess of a salt-forming acid in a solvent to form a salt or a hydrate or solvate thereof, of Formula (Ia), 2-(cyclohexylmethyl)-N-{2-[(2S)-1-methylpyrrolidin-2-yl]ethyl}-1,2,3,4-tetrahydroisoquinoline-7-sulfonamide acid addition salt; and e) optionally recrystallizing the product of step d).

A particular process of the invention for preparing 2-(cyclohexylmethyl)-N-{2-[(2S)-1-methylpyrrolidin-2-yl]ethyl}-1,2,3,4-tetrahydroisoquinoline-7-sulfonamide, or a pharmaceutically acceptable salt thereof, or a solvate or hydrate of a pharmaceutically acceptable salt, comprises:

a) reductively aminating 1,2,3,4-tetrahydroisoquinoline, or a salt thereof, with cyclohexanecarboxaldehyde in the presence of a reducing agent and in an organic solvent to give 2-cyclohexylmethyl-1,2,3,4-tetrahydroisoquinoline, or a salt thereof;

b) reacting 2-cyclohexylmethyl-1,2,3,4-tetrahydroisoquinoline, or a salt thereof, with excess chlorosulfonic acid optionally in the presence of a co-solvent to give 2-cyclohexylmethyl-1,2,3,4-tetrahydroisoquinoline-7-sulfonyl chloride HX salt, and optionally recrystallizing the 2-cyclohexylmethyl-1,2,3,4-tetrahydroisoquinoline-7-sulfonyl chloride HX salt;

c) coupling 2-cyclohexylmethyl-1,2,3,4-tetrahydroisoquinoline-7-sulfonyl chloride HX salt with (−)-2-(2-aminoethyl)-1-methylpyrrolidine in an organic solvent to form 2-(cyclohexylmethyl)-N-{2-[(2S)-1-methylpyrrolidin-2-yl]ethyl}-1,2,3,4-tetrahydroisoquinoline-7-sulfonamide;

d) optionally reacting 2-(cyclohexylmethyl)-N-{2-[(2S)-1-methylpyrrolidin-2-yl]ethyl}-1,2,3,4-tetrahydroisoquinoline-7-sulfonamide, with a stoichiometric amount or an excess of a salt-forming acid in a solvent to form a salt or a hydrate or solvate thereof; and e) optionally recrystallizing the product of step d).

For Scheme 1:

Step a) entails the formation of 2-cyclohexylmethyl-1,2,3,4-tetrahydroisoquinoline, or a salt thereof, by reacting 1,2,3,4-tetrahydroisoquinoline and cyclohexanecarboxaldehyde, in the presence of a reducing agent, such as formic acid, sodium triacetoxyborohydride, sodium borohydride, hydrogen with a catalyst, such as palladium on carbon, and the like, in a suitable organic solvent, such as methyl t-butyl ether, 1,2-dichloroethane, dichloromethane, or acetonitrile. This reaction is preferably performed at temperatures between about 8° C. and about 25° C. when the reducing agent is sodium triacetoxyborohydride, and at about 55° C. when the reducing agent is formic acid in methyl t-butyl ether. In one aspect, the 2-cyclohexylmethyl-1,2,3,4-tetrahydroisoquinoline is isolated as an acid addition salt, for example a hydrochloride salt.

2-Cyclohexylmethyl-1,2,3,4-tetrahydroisoquinoline-7-sulfonyl chloride HX salt is prepared in step b) by reacting 2-cyclohexylmethyl-1,2,3,4-tetrahydroisoquinoline, or a salt thereof, with excess chlorosulfonic acid, optionally in the presence of a co-solvent such as an aprotic, acid stable solvent, for example a halogenated solvent such as dichloromethane, chloroform, 1,2-dichloroethane, and the like; at temperatures preferably between about 2° C. and about 35° C. The product of this reaction is optionally recrystallized to remove positional isomers. Recrystallization solvents include, for example, acetonitrile with sulfuric acid.

Accordingly, one embodiment of the invention is the process for preparing 2-cyclohexylmethyl-1,2,3,4-tetrahydroisoquinoline-7-sulfonyl chloride HX salt by reacting 2-cyclohexylmethyl-1,2,3,4-tetrahydroisoquinoline with excess chlorosulfonic acid. Another embodiment of the invention is the process for preparing 2-(cyclohexylmethyl)-N-{2-[(2S)-1-methylpyrrolidin-2-yl]ethyl}-1,2,3,4-tetrahydroisoquinoline-7-sulfonamide comprising the step of reacting 2-cyclohexylmethyl-1,2,3,4-tetrahydroisoquinoline with excess chlorosulfonic acid. Another embodiment of the invention comprises optionally recrystallizing the product of the reaction between 2-cyclohexylmethyl-1,2,3,4-tetrahydroisoquinoline and excess chlorosulfonic acid. A particular embodiment is the product prepared by reacting 2-cyclohexylmethyl-1,2,3,4-tetrahydroisoquinoline with excess chlorosulfonic acid.

The coupling of 2-cyclohexylmethyl-1,2,3,4-tetrahydroisoquinoline-7-sulfonyl chloride HX and (−)-2-(2-aminoethyl)-1-methylpyrrolidine to prepare 2-(cyclohexylmethyl)-N-{2-[(2S)-1-methylpyrrolidin-2-yl]ethyl}-1,2,3,4-tetrahydroisoquinoline-7-sulfonamide in step c) is carried out in an organic solvent, for example dichloromethane, chloroform, 1,2-dichloroethane, methyl t-butyl ether, and toluene, and at a temperature between about 0° C. and about 35° C.

Therefore, one embodiment of the invention is the process for preparing 2-(cyclohexylmethyl)-N-{2-[(2S)-1-methylpyrrolidin-2-yl]ethyl}-1,2,3,4-tetrahydroisoquinoline-7-sulfonamide by coupling 2-cyclohexylmethyl-1,2,3,4-tetrahydroisoquinoline-7-sulfonyl chloride HX salt with (−)-2-(2-aminoethyl)-1-methylpyrrolidine. In one aspect, the coupling is carried out in an organic solvent.

Pharmaceutically acceptable salts of 2-(cyclohexylmethyl)-N-{2-[(2S)-1-methylpyrrolidin-2-yl]ethyl}-1,2,3,4-tetrahydroisoquinoline-7-sulfonamide, and hydrates and solvates thereof, include conventional, non-toxic salts of 2-(cyclohexylmethyl)-N-{2-[(2S)-1-methylpyrrolidin-2-yl]ethyl}-1,2,3,4-tetrahydroisoquinoline-7-sulfonamide, which can be formed with either inorganic acids such as hydrochloric acid, or organic acids such as benzoic acid, fumaric acid, oxalic acid and L-tartaric acid. A pharmaceutically acceptable salt can be obtained using standard procedures well known in the art, such as by reacting the compound of Formula (I) with stoichiometric amounts or with an excess of the desired salt-forming acid in a suitable solvent or various combinations of solvents. For example, an oxalate salt can be made by dissolving the compound of Formula (I) in ethanol and adding about 1.1 equivalents of oxalic acid, and allowing the salt to form. In one aspect of the invention, a fumarate salt is obtained. In a preferred aspect, the fumarate salt is a difumarate monohydrate salt.

The pharmaceutically acceptable salt of 2-(cyclohexylmethyl)-N-{2-[(2S)-1-methylpyrrolidin-2-yl]ethyl}-1,2,3,4-tetrahydroisoquinoline-7-sulfonamide, or hydrate or solvate thereof, is optionally recrystallized. Suitable recrystallization solvents include, for example isopropanol or ethanol in the presence of an anti-solvent such as toluene or acetone.

Another aspect of the invention are the processes described above further comprising the step of formulating 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof, or a solvate or hydrate of a pharmaceutically acceptable salt, with one or more pharmaceutically acceptable carrier agents, bulking agents, solvents, diluents and other excipients. In one aspect, the process comprises the step of formulating 2-(cyclohexylmethyl)-N-{2-[(2S)-1-methylpyrrolidin-2-yl]ethyl}-1,2,3,4-tetrahydroisoquinoline-7-sulfonamide difumarate monohydrate with one or more pharmaceutically acceptable carrier agents, bulking agents, solvents, diluents and other excipients.

The compound of Formula (IV), (−2-(2-aminoethyl)-1-methylpyrrolidine, may be prepared as outlined in Scheme 2.

Scheme 2

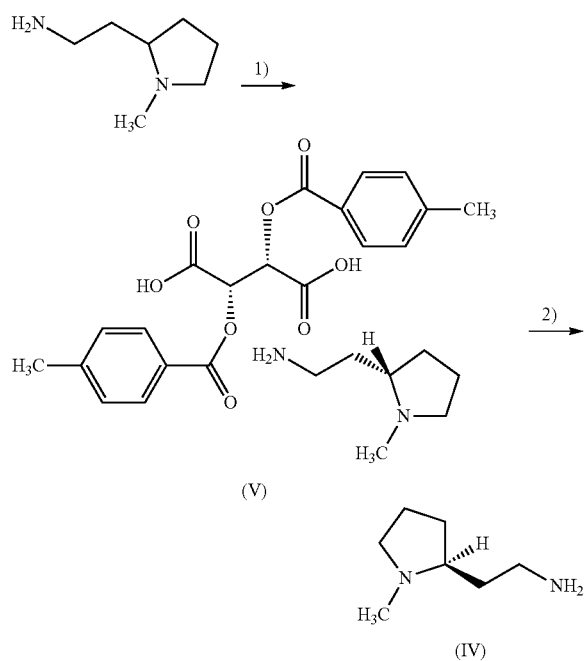

According to Scheme 2, step 1), racemic 2-(2-aminoethyl)-1-methylpyrrolidine is resolved by combining 2-(2-aminoethyl)-1-methylpyrrolidine with a chiral resolving agent, such as di-p-toluoyl-D-tartaric acid, in an alcohol, such as ethanol, methanol, isopropanol, and the like and combinations thereof including combinations with water. Preferably, the solvent is a combination of ethanol and water. The reaction is preferably performed at temperatures between about 0° C. and about the reflux temperature of the mixture, and more preferably, below about 100° C.

Racemic 2-(2-aminoethyl)-1-methylpyrrolidine starting material is commercially available (for example from Anichem LLC, American Custom Chemicals Inc., Acros, or Aldrich) or otherwise may be prepared according to procedures well know to those skilled in the art. (See, e.g., Turner, S. C.; Esbenshade, T. A.; Bennani, Y. L.; Hancock, A. A. Bioorg. Med. Chem. Lett. 2003, 13, 2131-2135).

Step 2) involves removing the resolving agent by dissolving the product of step 1), for example, (–)-2-(2-aminoethyl)-1-methylpyrrolidine, O,O'di-p-toluoyl-D-tartaric acid salt, in a two-phase mixture of a strong acid, such as concentrated HCl, HBr, H₂SO₄, H₃PO₄, and a non-polar solvent, such as t-butyl methyl ether, isopropyl acetate, and the like, at temperatures between about room temperature and about 100° C. The desired product may be isolated by removing the acid, such as the tartaric acid, with a non-polar solvent, such as t-butyl methyl ether or isopropylacetate. In one aspect, (–)-2-(2-aminoethyl)-1-methylpyrrolidine is isolated in aqueous solution as a salt. In another aspect, the acidic solution of (–)-2-(2-aminoethyl)-1-methylpyrrolidine salt is basified by the addition of a concentrated, strong base, such as sodium hydroxide, allowing the isolation of (–)-2-(2-aminoethyl)-1-methylpyrrolidine as the distillable free base.

The following examples present typical syntheses as described in Schemes 1 and 2. These examples are understood to be illustrative only and are not intended to limit the scope of the present invention in any way.

Example 1

Preparation of (–)-2-(2-Aminoethyl)-1-methylpyrrolidine

O,O'-Di-p-toluoyl-D-tartaric acid salt

A stock solution of aqueous ethanol was prepared by mixing ethanol (10370 mL) and water (2080 mL). A mixture of O,O'-di-p-tolouyl-D-tartaric acid (1624 g, 4.203 mol) and a portion of the above described stock solution of aqueous ethanol (9050 mL) was stirred at around 65° C. under a nitrogen atmosphere. Separately, racemic 2-(2-aminoethyl)-1-methylpyrrolidine (700 g, 5.35 mol) was dissolved in a portion of the aqueous ethanol stock solution (3400 mL). The amine solution was then added drop-wise to the tartaric acid solution so that the temperature was maintained at about 65° C. and no solids formed during the addition. The reaction was held at about 65° C. for no less than 30 min before being cooled to about 0° C. The precipitate was collected by filtration. A stream of nitrogen was pulled through the collected solid until no longer wet. The solid was recrystallized from ethanol (15950 mL)/water (2457 mL) affording the desired product as a colorless solid: 1322.4 g (44%), >99.5% ee.

Example 2

Preparation of (–)-2-(2-Aminoethyl)-1-methylpyrrolidine

A solution of HCl (296 mL, 3.55 mol) and water (517 mL) was added to a mixture of (–)-2-(2-aminoethyl)-1-methylpyrrolidine, O,O'-di-p-toluoyl-D-tartaric acid salt (900 g, 1.75 mol) and MTBE (3.2 L). After stirring for 45 minutes, the layers were separated. Additional MTBE (1.6 L) was added to the aqueous layer. After stirring for about 10 minutes, the layers were separated. With stirring, 50% aqueous NaOH (476 mL, 9.19 mol) was added to the aqueous acid layer over about 35 minutes. The mixture was stirred for about 35 minutes, then cooled to 10° C. The organic layer was separated and distilled at reduced pressure to provided 206 g (92%) of (–)-2-(2-Aminoethyl)-1-methylpyrrolidine.

Example 3

Preparation of a Compound of Formula (III)

2-Cyclohexylmethyl-1,2,3,4-tetrahydroisoquinoline HCl

A mixture of 1,2,3,4-tetrahydroisoquinoline (359.6 g, from Fluka), NaBH(OAc)₃ (686.7 g) and MTBE (5.4 L) was cooled and stirred as cyclohexanecarboxaldehyde (328.8 g, from Aldrich) was added over an approximately 30 minute period, maintaining the temperature of the reaction between about 8.8 and 21.1° C. over the course of the addition. The reaction was stirred at 20° C. for about 2 hours. A solution prepared from 50% aqueous NaOH (259 g) diluted to 1.1 L with H₂O was added with cooling, keeping the temperature at about 20° C. The reaction was stirred for 30 minutes, until no further hydrogen release was observed. The layers were separated, and the organic layer was washed with H₂O (2×2 L). The organic layer was dried with MgSO₄, and the drying agent was removed by filtration.

While stirring and maintaining the temperature at about 20° C., HCl gas (103 g) was bubbled into the solution, causing a precipitation of the hydrochloride salt. The salt was collected by filtration, washed with MTBE (4 L), and dried to provide 1637 g of the desired product.

Example 4

Preparation of a Compound of Formula (II)

2-(Cyclohexylmethyl)-1,2,3,4-tetrahydroisoquinoline-7-sulfonyl chloride HX

Chlorosulfonic acid (2.48 L) was added to a reactor containing 2-cyclohexylmethyl-1,2,3,4-tetrahydroisoquinoline HCl (1.10 kg) and $CH_2Cl_2$ (5.5 L) over a period of about one hour, while maintaining the temperature between −1.8° C. and 2.8° C. with cooling. Following the addition of the chlorosulfonic acid, the reaction was allowed to warm to 10° C., where it was held for approximately 2.5 hours. The reaction was warmed to 35° C. over 2 hours, then was held at 35° C. for 1 hour. The reaction was then maintained at 20° C. overnight. The $CH_2Cl_2$ was removed by distillation until the pot temperature reached 65° C. The reaction vessel was maintained at room temperature overnight. The mixture was slowly added to a suspension of MTBE (16.5 L) and seed crystals of 2-(cyclohexylmethyl)-1,2,3,4-tetrahydroisoquinoline-7-sulfonyl chloride HX (10 g), keeping the temperature between 20 to 25° C. After about 30 minutes, the product was collected by filtration affording an off-white solid. To isolate the desired product, the solid was mixed with acetonitrile (6.5 L) and concentrated $H_2SO_4$ (32 mL), and the mixture was heated to 70° C. The resulting solution was slowly cooled. A solid was isolated by filtration, rinsed with acetonitrile (2 L) and dried to provide 863.7 g of the desired product.

Seed crystals of 2-(cyclohexylmethyl)-1,2,3,4-tetrahydroisoquinoline-7-sulfonyl chloride HX can be obtained following general procedures known to those skilled in the art in view of the above-described procedure. Alternatively, 2-(cyclohexylmethyl)-1,2,3,4-tetrahydroisoquinoline-7-sulfonyl chloride HX can be readily prepared as described above without the use of seed crystals.

Example 5

Preparation of a Compound of Formula (I)

2-(Cyclohexylmethyl)-N-{2-[(2S)-1-methylpyrrolidin-2-yl]ethyl}-1,2,3,4-tetrahydroisoquinoline-7-sulfonamide A slurry of 2-(cyclohexylmethyl)-1,2,3,4-tetrahydroisoquinoline-7-sulfonyl chloride HX (477.7 g) and $CH_2Cl_2$ (4.78 L) was cooled to about 5° C. A solution (−)-2-(2-aminoethyl)-1-methylpyrrolidine (185.1 g) in $CH_2Cl_2$ (370 mL) was added at a rate that kept the temperature below 9° C. Upon completion of the addition, the reaction was warmed to 25° C. After about 4 hours, the solvent was removed at reduced pressure, leaving a viscous oil. After standing over the weekend under $N_2$ atmosphere in a cold room at 4° C., the oil was treated with a solution of $K_2CO_3$ (452 g) in water (2.8 L) followed by EtOAc (6.5 L). The two-phase mixture was stirred for 30 minutes, before the aqueous layer was removed. The organic layer was washed with water (3×3 L). The solvent was evaporated at reduced pressure leaving 488.5 g of 2-(cyclohexylmethyl)-N-{2-[(2S)-1-methylpyrrolidin-2-yl]ethyl}-1,2,3,4-tetrahydroisoquinoline-7-sulfonamide as a viscous oil.

Example 6

Preparation of a Compound of Formula (Ia)

2-(Cyclohexylmethyl)-N-{2-[(2S)-1-methylpyrrolidin-2-yl]ethyl}-1,2,3,4-tetrahydroisoquinoline-7-sulfonamide difumarate monohydrate A solution of 2-(cyclohexylmethyl)-N-{2-[(2S)-1-methylpyrrolidin-2-yl]ethyl}-1,2,3,4-tetrahydroisoquinoline-7-sulfonamide (532 g, 1.27 mol) in SDA 3C ethanol (1056 mL) was added to a suspension of fumaric acid (302 g, 2.60 mol) in water (624 mL). The resulting solution was diluted with acetone (4 L) then cooled and seeded with milled 2-(cyclohexylmethyl)-N-{2-[(2S)-1-methylpyrrolidin-2-yl]ethyl}-1,2,3,4-tetrahydroisoquinoline-7-sulfonamide difumarate monohydrate (4.2 g). After seeding, the mixture was stirred to allow crystal growth then further diluted with acetone (1990 mL). After cooling, the product was collected by filtration and washed with acetone (1.500 L). Filtration was conducted by portionwise loading of acetone into the filter-dryer. After loading of each portion of acetone (1.5 L) stirring was turned on at 2.6 rpm to ensure good contact between product and acetone. The product was dried in a vacuum oven at 40° C. with nitrogen purge and vacuum (residual pressure 400 mBar) then allowed to re-hydrate at room temperature in the air to yield 684.7 g (85.8%) of 2-(cyclohexylmethyl)-N-{2-[(2S)-1-methylpyrrolidin-2-yl]ethyl}-1,2,3,4-tetrahydroisoquinoline-7-sulfonamide difumarate monohydrate.

Seed crystals of 2-(cyclohexylmethyl)-N-{2-[(2S)-1-methylpyrrolidin-2-yl]ethyl}-1,2,3,4-tetrahydroisoquinoline-7-sulfonamide difumarate monohydrate can be obtained following general procedures known to those skilled in the art. Alternatively, 2-(cyclohexylmethyl)-N-{2-[(2S)-1-methylpyrrolidin-2-yl]ethyl}-1,2,3,4-tetrahydroisoquinoline-7-sulfonamide difumarate monohydrate can readily be prepared as described above without the use of seed crystals.

What is claimed is:

1. A process for preparing 2-(cyclohexylmethyl)-N-{2-[(2S)-1-methylpyrrolidin-2-yl]ethyl}-1,2,3,4-tetrahydroisoquinoline-7-sulfonamide, or a pharmaceutically acceptable salt thereof, or a solvate or hydrate of a pharmaceutically acceptable salt comprising:
    a) reductively aminating 1,2,3,4-tetrahydroisoquinoline, or a salt thereof, with cyclohexanecarboxaldehyde to give 2-cyclohexylmethyl-1,2,3,4-tetrahydroisoquinoline, or a salt thereof;
    b) reacting 2-cyclohexylmethyl-1,2,3,4-tetrahydroisoquinoline, or a salt thereof, with excess chlorosulfonic acid to give 2-cyclohexylmethyl-1,2,3,4-tetrahydroisoquinoline-7-sulfonyl chloride HX salt, and optionally recrystallizing the 2-cyclohexylmethyl-1,2,3,4-tetrahydroisoquinoline-7-sulfonyl chloride HX salt;
    c) coupling 2-cyclohexylmethyl-1,2,3,4-tetrahydroisoquinoline-7-sulfonyl chloride HX salt with (−)-2-(2-aminoethyl)-1-methylpyrrolidine to form 2-(cyclohexylmethyl)-N-{2-[(2S)-1-methylpyrrolidin-2-yl]ethyl}-1,2,3,4-tetrahydroisoquinoline-7-sulfonamide;
    d) optionally reacting 2-(cyclohexylmethyl)-N-{2-[(2S)-1-methylpyrrolidin-2-yl]ethyl}-1,2,3,4-tetrahydroisoquinoline-7-sulfonamide with a stoichiometric amount or an excess of a salt-forming acid in a solvent to form a salt or a hydrate or solvate thereof; and
    e) optionally recrystallizing the product of step d).

2. The process according to claim 1, wherein the reductive amination of step a) is performed in an organic solvent in the presence of a reducing agent.

3. The process according to claim 2, wherein the reducing agent is selected from the group consisting of sodium triacetoxyborohydride, sodium borohydride, formic acid, and hydrogen with a catalyst.

4. The process according to claim 1 wherein the reaction of step b) is performed in the presence of a co-solvent.

5. The process according to claim 4, wherein the co-solvent is selected from the group consisting of dichloromethane, chloroform, and 1,2-dichloroethane.

6. The process according to claim 1, wherein step c) is performed in the presence of an organic solvent.

7. The process according to claim 6, wherein the organic solvent is selected from the group consisting of dichloromethane, chloroform, 1,2-dichloroethane, methyl t-butyl ether, and toluene.

8. The process according to claim 1, wherein the salt formed in step d) is a pharmaceutically acceptable salt.

9. The process according to claim 1, further comprising formulating 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof, or a solvate or hydrate of a pharmaceutically acceptable salt, with one or more pharmaceutically acceptable carrier agents, bulking agents, solvents, diluents and other excipients.

10. The process according to claim 1, wherein the salt-forming acid in step d) is fumaric acid to provide 2-(cyclohexylmethyl)-N-{2-[(2S)-1-methylpyrrolidin-2-yl]ethyl}-1,2,3,4-tetrahydroisoquinoline-7-sulfonamide difumarate monohydrate.

11. The process according to claim 10, further comprising formulating 2-(cyclohexylmethyl)-N-{2-[(2S)-1-methylpyrrolidin-2-yl]ethyl}-1,2,3,4-tetrahydroisoquinoline-7-sulfonamide difumarate monohydrate with one or more pharmaceutically acceptable carrier agents, bulking agents, solvents, diluents and other excipients.

12. The process according to claim 1, comprising
   a) reductively aminating 1,2,3,4-tetrahydroisoquinoline, or a salt thereof, with cyclohexanecarboxaldehyde in the presence of a reducing agent and in an organic solvent to give 2-cyclohexylmethyl-1,2,3,4-tetrahydroisoquinoline, or a salt thereof;
   b) reacting 2-cyclohexylmethyl-1,2,3,4-tetrahydroisoquinoline, or a salt thereof, with excess chlorosulfonic acid optionally in the presence of a co-solvent to give 2-cyclohexylmethyl-1,2,3,4-tetrahydroisoquinoline-7-sulfonyl chloride HX salt, and optionally recrystallizing the 2-cyclohexylmethyl-1,2,3,4-tetrahydroisoquinoline-7-sulfonyl chloride HX salt;
   c) coupling 2-cyclohexylmethyl-1,2,3,4-tetrahydroisoquinoline-7-sulfonyl chloride HX salt with (−)-2-(2-aminoethyl)-1-methylpyrrolidine in an organic solvent to form 2-(cyclohexylmethyl)-N-{2-[(2S)-1-methylpyrrolidin-2-yl]ethyl}-1,2,3,4-tetrahydroisoquinoline-7-sulfonamide;
   d) optionally reacting 2-(cyclohexylmethyl)-N-{2-[(2S)-1-methylpyrrolidin-2-yl]ethyl}-1,2,3,4-tetrahydroisoquinoline-7-sulfonamide with a stoichiometric amount or an excess of a salt-forming acid in a solvent to form a pharmaceutically acceptable salt or a hydrate or solvate thereof; and
   e) optionally recrystallizing the product of step d).

13. The process according to claim 12, further comprising formulating 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof, or a solvate or hydrate of a pharmaceutically acceptable salt, with one or more pharmaceutically acceptable carrier agents, bulking agents, solvents, diluents and other excipients.

14. The process according to claim 12, wherein the salt-forming acid in step d) is fumaric acid to provide 2-(cyclohexylmethyl)-N-{2-[(2S)-1-methylpyrrolidin-2-yl]ethyl}-1,2,3,4-tetrahydroisoquinoline-7-sulfonamide difumarate monohydrate.

15. The process according to claim 14, further comprising formulating 2-(cyclohexylmethyl)-N-{2-[(2S)-1-methylpyrrolidin-2-yl]ethyl}-1,2,3,4-tetrahydroisoquinoline-7-sulfonamide difumarate monohydrate with one or more pharmaceutically acceptable carrier agents, bulking agents, solvents, diluents and other excipients.

16. A process for preparing 2-(cyclohexylmethyl)-N-{2-[(2S)-1-methylpyrrolidin-2-yl]ethyl}-1,2,3,4-tetrahydroisoquinoline-7-sulfonamide comprising the step of reacting 2-cyclohexylmethyl-1,2,3,4-tetrahydroisoquinoline with excess chlorosulfonic acid.

17. The process according to claim 16 wherein the reaction is performed in the presence of a co-solvent.

18. A process for preparing 2-(cyclohexylmethyl)-N-{2-[(2S)-1-methylpyrrolidin-2-yl]ethyl}-1,2,3,4-tetrahydroisoquinoline-7-sulfonamide by coupling 2-cyclohexylmethyl-1,2,3,4-tetrahydroisoquinoline-7-sulfonyl chloride HX salt with (−)-2-(2-aminoethyl)-1-methylpyrrolidine.

* * * * *

UNITED STATES PATENT AND TRADEMARK OFFICE
CERTIFICATE OF CORRECTION

PATENT NO.       : 8,779,145 B2
APPLICATION NO.  : 13/600975
DATED            : July 15, 2014
INVENTOR(S)      : Steven Elenbaas Page 1 of 1

It is certified that error appears in the above-identified patent and that said Letters Patent is hereby corrected as shown below:

On the Title Page, Item (54) and in the Specification, Column 1, lines 1-4, title should read:

PROCESS FOR THE PREPARATION OF 2-(CYCLOHEXYLMETHYL)-
N-{2-[(2S)-1-METHYLPYRROLIDIN-2-YL]ETHYL}-1,2,3,4-
TETRAHYDROISOQUINOLINE-7-SULFONAMIDE

Signed and Sealed this
Seventeenth Day of February, 2015

Michelle K. Lee
*Deputy Director of the United States Patent and Trademark Office*